United States Patent [19]

Rabenau et al.

[11] Patent Number: 5,476,368
[45] Date of Patent: Dec. 19, 1995

[54] STERILE FLUID PUMP DIAPHRAGM CONSTRUCTION

[75] Inventors: Richard Rabenau, Birmingham; Stephen P. Lisak; Terry B. Kehne, both of Arab; Richard M. Davis, Guntersville, all of Ala.

[73] Assignee: Ryder International Corporation, Arab, Ala.

[21] Appl. No.: 196,388

[22] Filed: Feb. 15, 1994

Related U.S. Application Data

[63] Continuation-in-part of Ser. No. 932,752, Aug. 20, 1992, Pat. No. 5,344,292.

[51] Int. Cl.⁶ .................................................. F04B 43/02
[52] U.S. Cl. ............................................ 417/395; 417/540
[58] Field of Search .......................... 417/395, 383–388, 417/63, 540

[56] References Cited

U.S. PATENT DOCUMENTS

| | | | |
|---|---|---|---|
| 2,662,478 | 12/1953 | Surre | 417/63 |
| 3,030,892 | 9/1962 | Piccardo | 417/384 |
| 3,131,638 | 5/1964 | Wilson et al. | 92/47 |
| 3,807,906 | 4/1974 | Breit | 417/63 |
| 4,303,376 | 12/1981 | Sickmann | 417/360 |
| 4,479,761 | 10/1984 | Bilstad et al. | 417/395 |
| 4,573,883 | 3/1986 | Noon et al. | 417/394 |
| 4,639,245 | 1/1987 | Pastrone et al. | 604/152 |
| 4,818,186 | 4/1989 | Pastrone et al. | 417/63 |
| 4,881,876 | 11/1989 | Laziou | 417/63 |
| 4,898,584 | 2/1990 | Borsanyi et al. | 604/153 |
| 4,903,655 | 2/1990 | Vonderau et al. | 417/540 |
| 4,934,902 | 6/1990 | Mantell | 417/63 |
| 4,979,760 | 10/1990 | Bilstad et al. | 417/395 |
| 5,062,776 | 11/1990 | Story et al. | 417/63 |
| 5,074,757 | 12/1991 | Moon | 417/395 |
| 5,171,134 | 12/1992 | Mercart et al. | 417/540 |
| 5,188,515 | 2/1993 | Horn | 417/63 |

FOREIGN PATENT DOCUMENTS

| | | | |
|---|---|---|---|
| 1305549 | 4/1962 | France | 417/384 |

Primary Examiner—Richard A. Bertsch
Assistant Examiner—Peter G. Korytnyk
Attorney, Agent, or Firm—Trexler, Bushnell, Giangiorgi & Blackstone, Ltd.

[57] ABSTRACT

A fluid pumping assembly for particular use in delivery of sterile fluid used in surgical procedures, includes a pump control structure to which a replaceable fluid pumping cartridge is connected and disconnected to provide convenient replacement and disposability of the cartridge. The pump cartridge is self-contained in that it includes a fluid pump which is adapted for automatic connection to a pump drive structure when the cartridge is inserted into the assembly, so that the sterile fluid is pumped only through the pumping cartridge and fluid flow is entirely isolated from the pump control structure to ensure that the fluid is maintained sterile during pumping. The cartridge can include a selectively activated pulsation control to enable discharging the fluid from the cartridge in either a continuous flow or pulsating flow of the fluid. The cartridge can also include fluid flow dampening and safety vent features. The pump control structure can provide a pneumatic drive system which cycles pressurized air to drive the pump. A pneumatic control valve provides cycled switching of alternating air pressure and exhaust communication with the pump.

18 Claims, 10 Drawing Sheets

▨ PRESSURIZED (AIR FLOW IN)
▨ EXHAUSTED (AIR FLOW OUT)

STERILE FLUID PUMP DIAPHRAGM CONSTRUCTION

CROSS REFERENCE TO RELATED APPLICATION

This Application is a Continuation-In-Part of Application Ser. No. 07/932,752, filed Aug. 20, 1992 now U.S. Pat. No. 5,344,292, the complete disclosure of which is incorporated by reference herein.

BACKGROUND OF THE INVENTION

This invention relates to fluid pump systems, and more particularly relates to improved fluid delivery apparatus adapted for use in surgical procedures to deliver a continuous supply of sterile fluid, such as saline, wherein a replaceable pump cartridge is employed.

In surgical procedures, particularly laparoscopic procedures, irrigation solution, typically sterile saline is directed under pressure to irrigate the surgical site. In order to ensure the sterile condition of the pressurized fluid, the fluid pump and delivery systems must also be in sterile condition which has required the effort and attention of skilled personnel to prepare sterilized equipment, and to sterilize the pumping apparatus preparatory to each procedure.

In addition, the surgeon often prefers to employ a pulsating stream of the pressurized irrigation fluid, for example, to facilitate disintegration of clots or dislodgment of severed tissue. Heretofore, irrigation pumping units have been limited to either a continuous irrigation stream or a pulsating stream, requiring use of multiple equipment to accommodate choice of irrigation stream condition. These disadvantages are eliminated by the system and apparatus improved in accordance with the present invention.

SUMMARY OF THE INVENTION

According to the present invention, a fluid pumping assembly for particular use in delivery of sterile fluid used in surgical procedures includes a conveniently replaceable and disposable cartridge adapted for connection to and disconnection from a pump drive structure which is isolated from the fluid flow through the cartridge to ensure that the fluid is maintained sterile during pumping. Preferably, the cartridges are disposable so that there is no need to sterilize the apparatus between surgical procedures.

In one embodiment, the cartridge includes dampening structure for directing dampening fluid in opposition to flow pulses of the sterile fluid in order to produce dampening modulation of the sterile fluid flow pulses. The fluid dampening structure can be operated selectively to control the sterile fluid pulsation to enable discharging the sterile fluid from the cartridge in either a continuous flow or pulsating flow, under selection by the surgeon. The cartridge can also include pump structure adapted for connection, for example, to a pneumatic drive assembly of the pump control structure.

The cartridge can also include a pumping chamber having a pump diaphragm for pumping the sterile fluid, and a dampening chamber having a separate dampening or control diaphragm capable of resiliently oscillating and absorbing fluid flow pulses from the pump diaphragm to produce modulated flow of the sterile fluid from the cartridge.

An additional aspect of the invention includes a back-to-back, dual diaphragm pumping structure housed within the cartridge so that one of the diaphragms isolates the sterile pump fluid from the pumping drive forces on the other diaphragm. A venting passageway is provided between the first and second diaphragms in order to provide relief venting through the passageway. Thus, should either diaphragm fail, any potential leakage of the sterile fluid or the pneumatic drive gas, is contained and cross contamination is prevented, preserving the sterile nature of the irrigation solution.

Another aspect of the invention includes a pneumatic drive system which cycles pressurized air to drive oscillation of the pump diaphragm. A pneumatic control valve provides cycled switching of alternating air pressure and exhaust communication with the pump diaphragm. The control valve can be adjustably piloted to enable variable frequency of the cycled air pressure drive and the pump diaphragm oscillation.

DESCRIPTION OF THE ILLUSTRATED EMBODIMENTS

Figure 1:
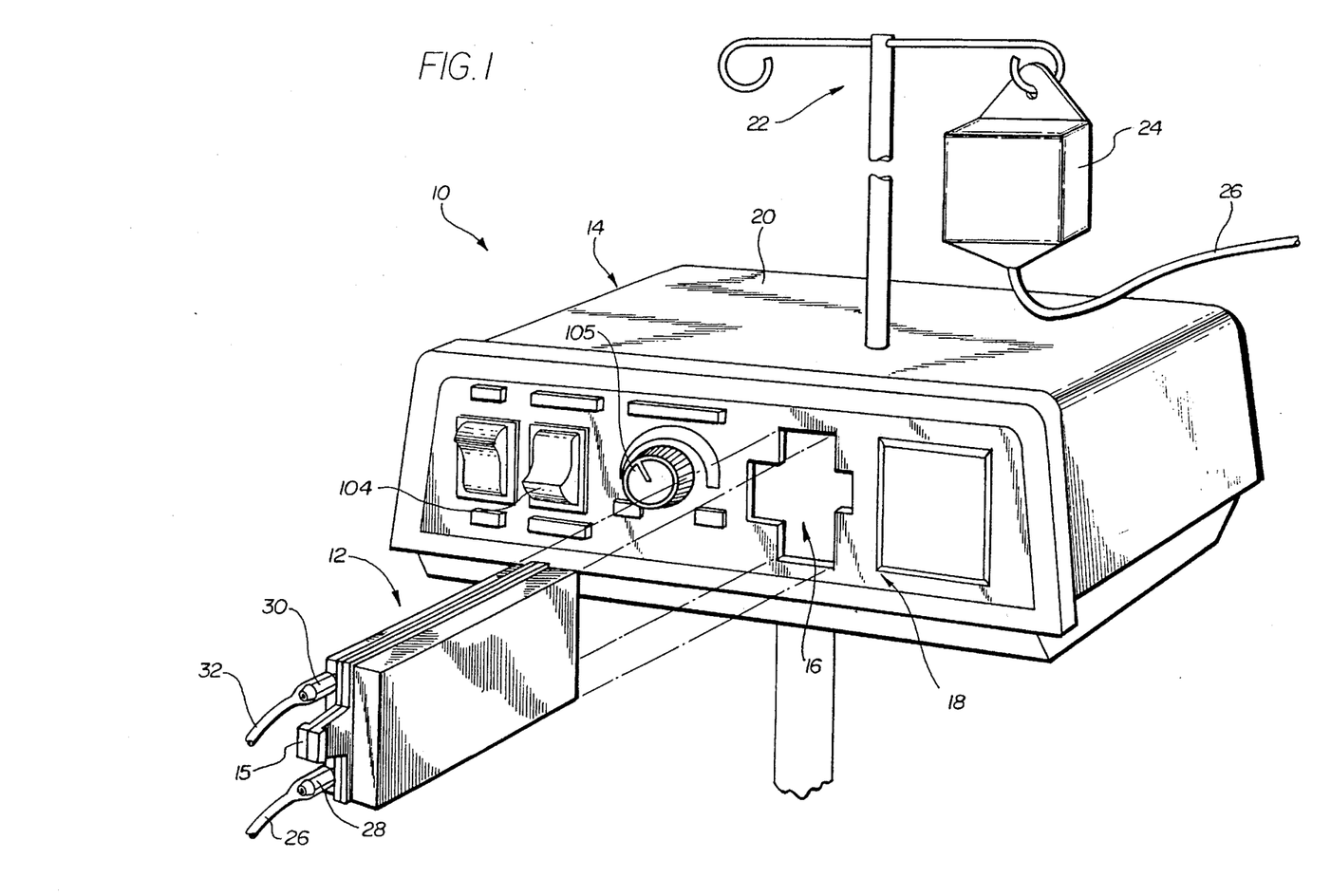
FIG. 1 is a perspective view of one embodiment of a fluid pumping assembly and cartridge in accordance with the present invention.

Referring to FIG. 1, a fluid pumping system generally designated by reference character 10 is illustrated, in which one embodiment of a pumping cartridge 12 is illustrated in position for installation into the system in which the cartridge 12 is installed for convenient, single use, and facilitated replacement with a succeeding sterile cartridge for a subsequent surgical procedure. The cartridge 12 is manually inserted or removed from the pump housing 14 through a receptive aperture 16 formed in the face plate 18, and gripped by handle 15. The cover 20 of the pump housing 14 supports a typical hanger 22 on which is hung one or two fluid supply bags 24 containing, for example, sterile saline irrigation solution which is to be pumped by the system 10 for use such as in pressurized surgical irrigation. The delivery tube 26 from the bag 24 is connected to the fluid intake nipple 28 on the cartridge 12. The fluid is pumped and flows through only the cartridge 12 so that the pressurized fluid effluent from the cartridge 12 flows from the discharge nipple 30 for delivery through the connected line 32 to a laparoscopic or other surgical instrument (not shown). The fluid flow through the cartridge 12 is thus isolated from the remainder of the system 10 which therefore need not be sterilized, and the sterile cartridge 12 maintains sterile condition of the fluid since the convenient installation and removal allow the cartridges 12 to be disposable and a new, sterile cartridge 12 is used for fluid pumping in any subsequent surgical procedure using the system 10.

Figures 2, 3:
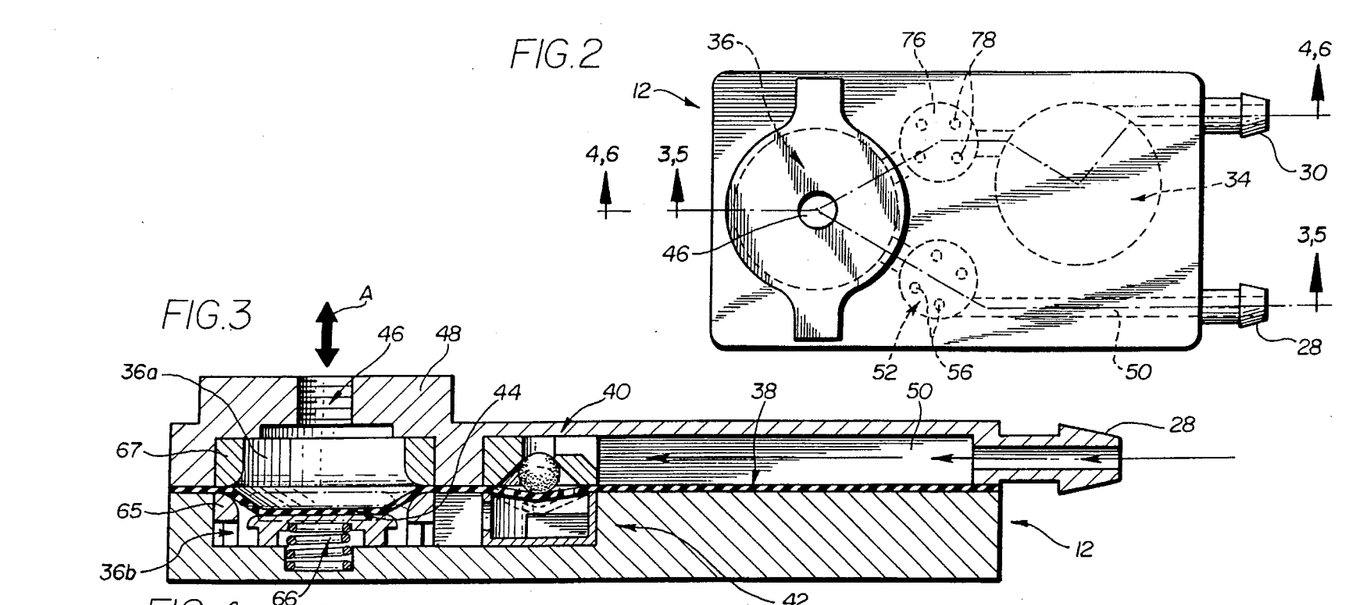
FIG. 2 is a plan view of one embodiment of the pumping cartridge shown in FIG. 1, in accordance with the invention.
FIG. 3 is a sectional view of the cartridge taken along a plane indicated by line 3—3 in FIG. 2.
Figure 4:
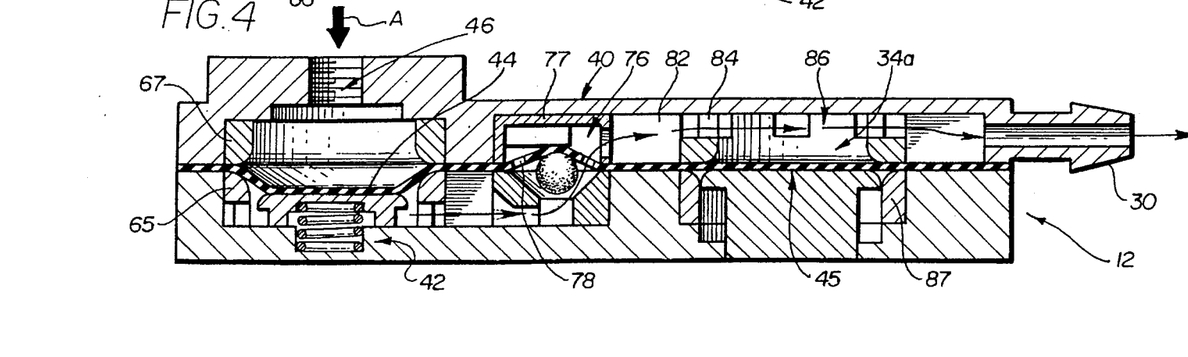
FIG. 4 is a sectional view of the cartridge taken along a plane indicated by line 4—4 in FIG. 2, and illustrating pressurized fluid discharge from the cartridge with completion of a pumping portion of the cycled pump action within the cartridge.

Referring now to FIGS. 2–7, one version or embodiment of a design for cartridge 12 is illustrated, which embodiment provides pumping of the fluid selectively in either a continuous or pulsating flow. The selective pulsating flow is enabled by including in the cartridge 12 an accumulator chamber 34 which receives the pressurized discharge flow from the pump chamber 36. In the illustrated embodiment, the cartridge 12 has a resilient diaphragm 38 of suitable elastomeric material which is retained (by suitable fastening means, not shown) between housing portions or sections generally designated by reference characters 40 and 42. A portion 44 of the diaphragm 38 provides a resilient pump diaphragm which reciprocates within the pumping chamber 36 formed by aligned cylindrical cavities 36a and 36b respectively formed in housing portions 40 and 42. Referring briefly to FIGS. 3 and 4, the reciprocating, pump diaphragm portion 44 is driven by cycled, pneumatic air pressure indicated by arrow A received directly through an air drive conduit 46 which passes through a boss 48 on the wall of the housing portion 40. The air pressure A is cycled by controls more fully described hereinafter.

Figure 5:
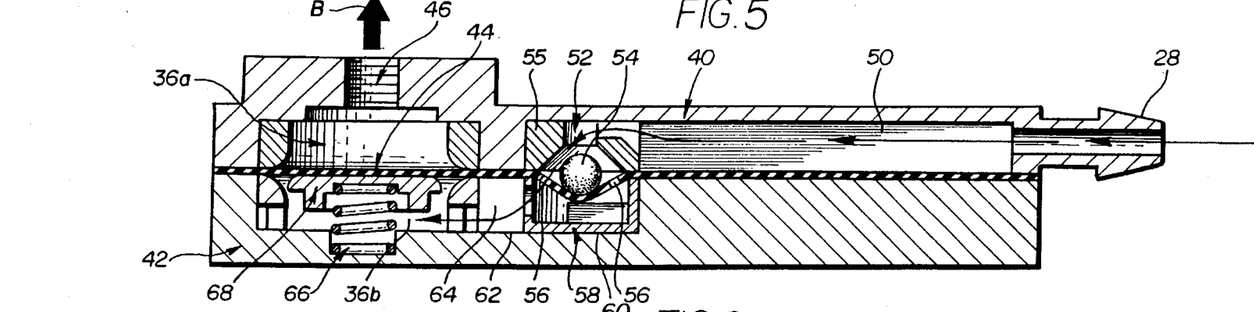
FIG. 5 is a sectional view of the cartridge taken along a plane indicated by line 5—5 in FIG. 2, illustrating fluid drawn into the cartridge with the return portion of the cycled pumping action.

Referring to FIG. 5, supply fluid is drawn through nipple 28 into the lead conduit 50 from which the flow passes through open intake check valve 52 by dislodgment of the ball 54 from the throat of insert 55 enabling the fluid to pass through the four, through diaphragm apertures 56 (FIGS. 2 and 3). The fluid is drawn through the diaphragm apertures 56 into the intake check valve insert 58 seated within the intake check valve cavity 60 formed in the housing portion 42. The insert 58 has an outlet aperture 62 which leads through the housing channel 64 into the pump cavity 36b to which the flow is drawn by the return stroke of the reciprocating diaphragm pump portion 44 assisted by the expansion of the return spring 66 and flange 68 engaged against the diaphragm portion 44, during the pneumatic exhaust portion of the cycled air drive indicated by arrow B. At the same time, the return stroke of the diaphragm pump portion 44 also draws fluid from channel 69 and closes the ball 70 against the diaphragm portion 44, during the pneumatic exhaust portion of the cycled air drive indicated by arrow B. At the same time, the return stroke of the diaphragm pump portion 44 also draws fluid from channel 69 and closes the ball 70 against the discharge check valve insert 72 seated in the cavity 74 of the housing portion 42. The closure by the check ball 70 causes interruption of flow through the discharge check valve 76 and diaphragm apertures 78, and the resultant reduction of pressure in the accumulator cavity portion 34a produces consequent pulse interruption in the discharge flow from the nipple 30 in the selected pulse flow operation of the cartridge 12.

In the alternative continuous flow (FIG. 7), a selective withdrawal of the accumulator pressure plate 80, controlled as more fully described hereinafter, enables the accumulator diaphragm portion 45 to be resiliently displaced into the accumulator cavity portion 34b within the housing portion 42; when free to displace, the accumulator diaphragm portion 45 will absorb the cycled pulses of increased fluid flow pressure generated by the power stroke of the pump diaphragm portion 44 as shown in FIG. 4. As best viewed in FIG. 4, the power stroke flow uplifts the ball 70 and flows through the discharge check valve 76, diaphragm aperture 78, flow director insert 77, housing channel 82, and flow gap 84 in the accumulator insert 86 as the flow enters the accumulator cavity portion 34a. The accumulator inserts 86 and 87, and the similar pump chamber inserts 65 and 67 provide curved periphery for wear protection of the fixed rim of the diaphragm portions 45 and 44, respectively.

Figure 6:
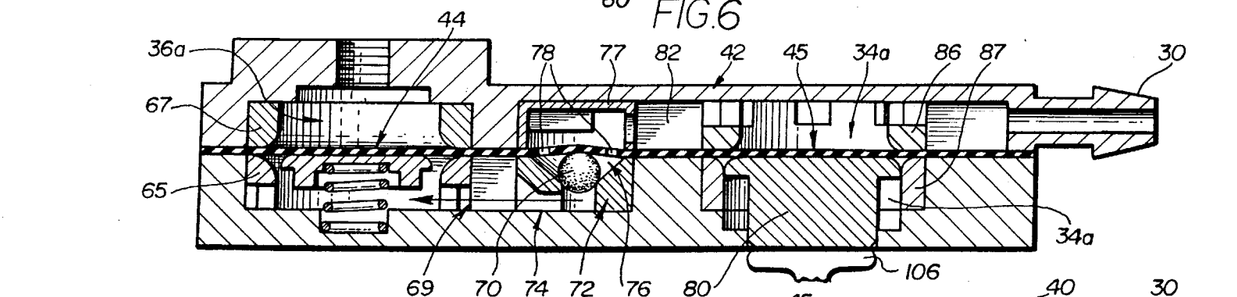
FIG. 6 is a sectional view taken along a plane indicated by line 6—6 in FIG. 2, and illustrating pause in flow between pulses in pulsating flow operation of the cartridge.

On the return stroke of the pump diaphragm portion 44 as shown in FIG. 6, the accumulator diaphragm portion 45 will resiliently unflex so as to maintain flow pressure on the fluid in the accumulator and prevent any interruption of discharged flow from the nipple 30.

Figure 7:
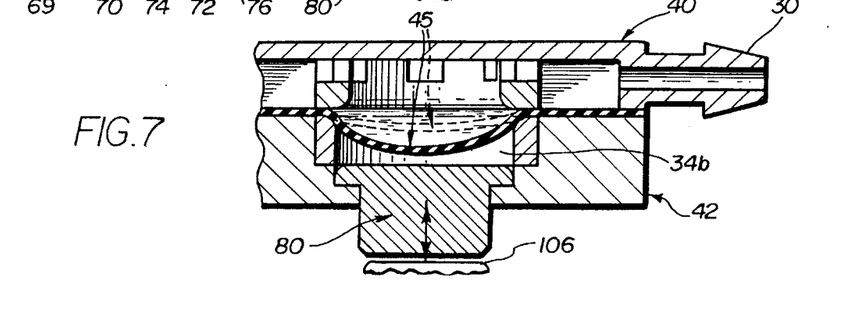
FIG. 7 is a fragmentary sectional view of the accumulator chamber shown in FIG. 6 and showing the selective operation of the accumulator chamber to enable continuous flow from the cartridge.
Figure 8:
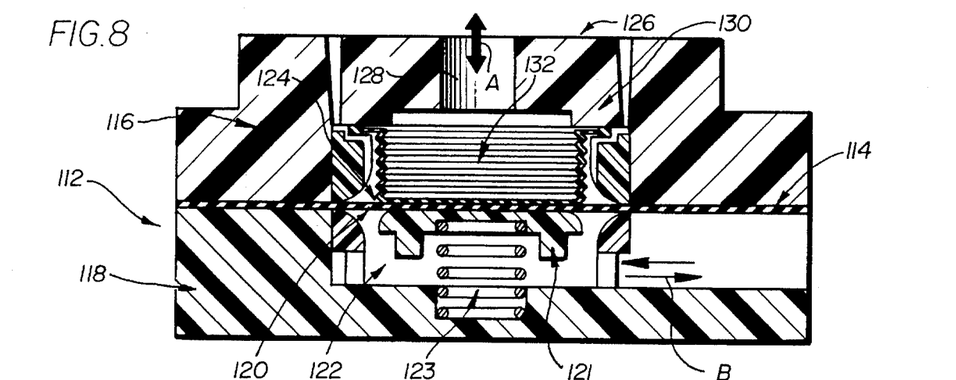
FIG. 8 is a fragmentary sectional view of a second embodiment of a pumping cartridge in accordance with the invention.

The choice of either continuous or pulsed fluid discharge and delivery from the cartridge 12 is controlled by switch 104 which will selectively actuate displacement of a plunger 106 from an air cylinder (not shown) to drive the accumulator pressure plate 80 from the position shown in FIG. 7 to the position shown in FIG. 6 into engagement with the accumulator diaphragm portion 45 which holds it stationary without displacement resulting in pulsating flow from the cartridge 12. The alternative continuous flow operation of the cartridge 12 is controlled by retracting the plunger 106 to allow withdrawal of the accumulator pressure plate 80.

In a second embodiment illustrated in FIGS. 8–13, the cartridge 112 has a main, resilient diaphragm 114 which is retained (by suitable fastening means, not shown) between housing portions generally designated by reference characters 116 and 118. A portion 120 of the main diaphragm 114 provides a resilient fluid pump which reciprocates within a pumping chamber formed by aligned cylindrical cavities 122 and 124 respectively formed in the housing portions 118 and 116. The cartridge pump assembly generally designated by reference character 126 is driven by cycled, pneumatic (or hydraulic) pressure indicated by arrow A delivered directly through air drive conduit 128 which passes through a boss 130 on the wall of the cartridge housing portion 116.

Figure 21:
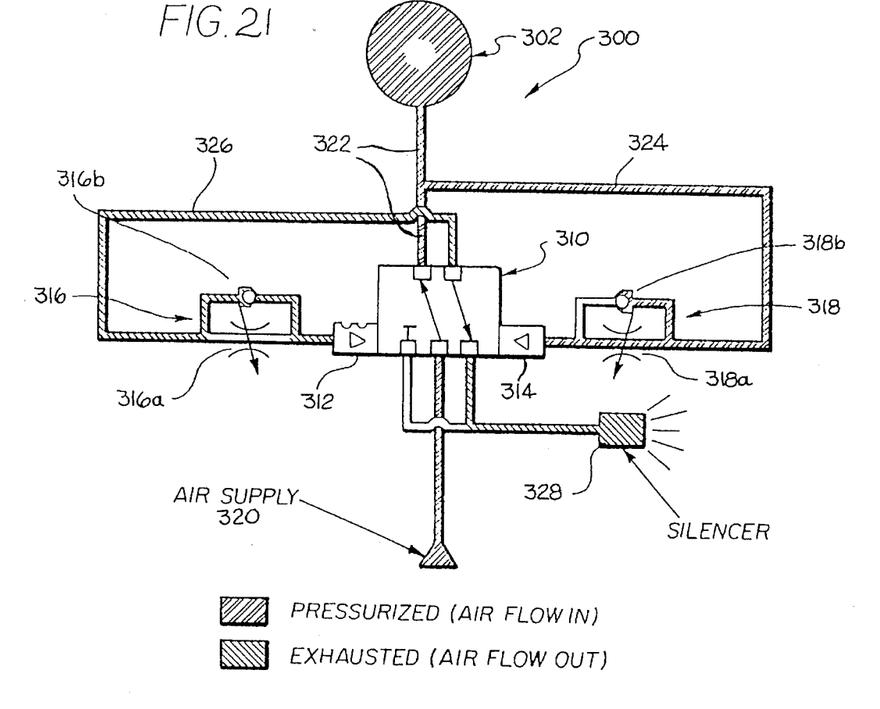
FIGS. 21 and 22 are pneumatic circuit flow diagrams of a second embodiment of an actuator to drive pump operation of cartridges in accordance with the present invention.
Figure 22:
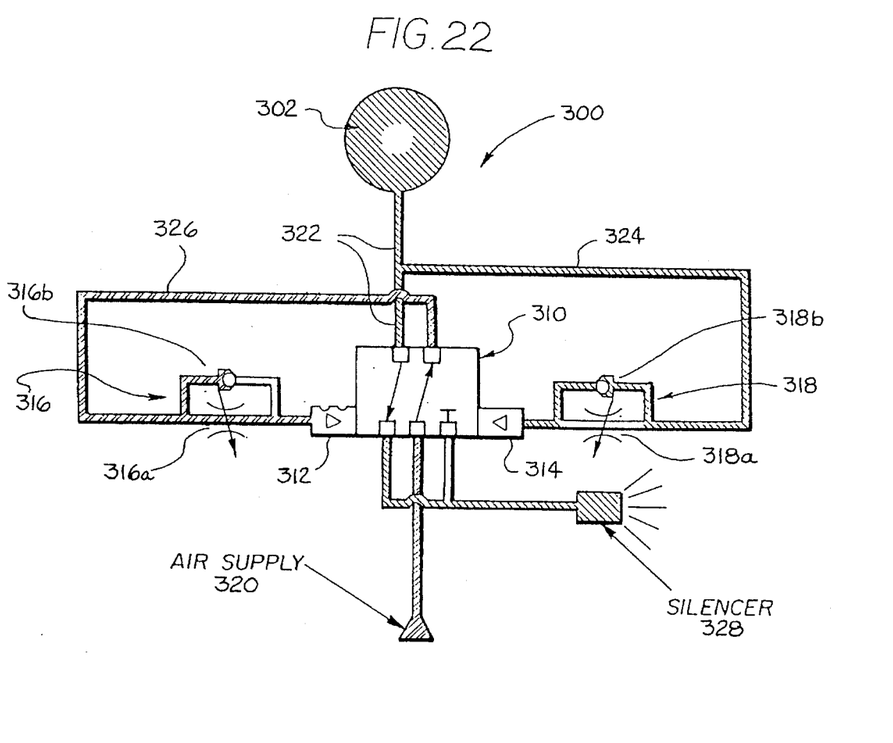

The cartridge 112 can selectively produce either a continuous or a pulsating discharge flow, for example, by including in the cartridge structure an accumulator chamber (not shown) which receives the pressurized discharge flow from the pump structure 126, as more fully described herein with reference to the first cartridge embodiment, and similarly provided in the third cartridge embodiment described hereinafter with reference to FIGS. 15–19. Pneumatic drive control such as shown in FIG. 21 or FIGS. 21–22 can be provided within a control housing 14 (FIG. 1).

The pump diaphragm portion 120 is supported on a movable return flange 121 and return spring 123 to assist the exhaust cycle of the reciprocating pneumatic pump assembly 126. As best illustrated by comparison of FIGS. 2 and 3, the cartridge pump structure 126 has a secondary, pneumatic diaphragm 132 which elastically receives impingement of the cycled pneumatic drive pressure and engages the diaphragm portion 120 for resiliently transmitting the pneumatic drive pressure to produce the pumping of the sterile, surgical fluid from the pump chamber cavity 122 along the discharge flow path designated by arrow B in FIG. 9.

Figure 10:
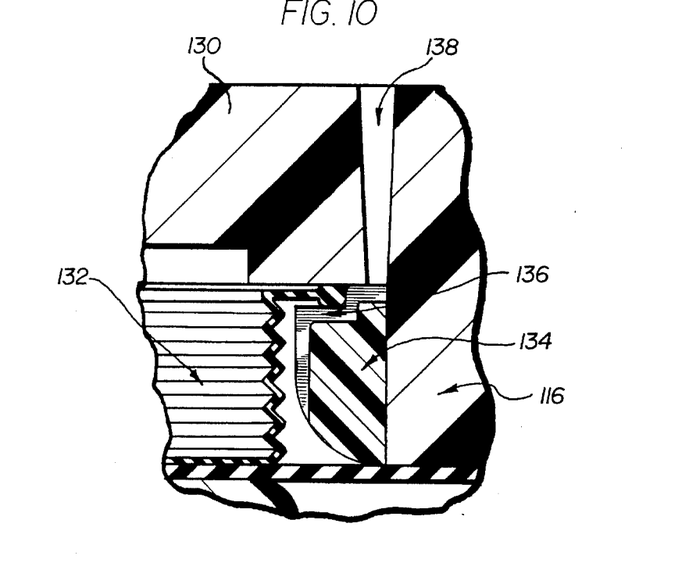
FIG. 10 is an enlarged fragmentary sectional view of the pumping cartridge shown in FIGS. 8 and 9.
Figure 11:
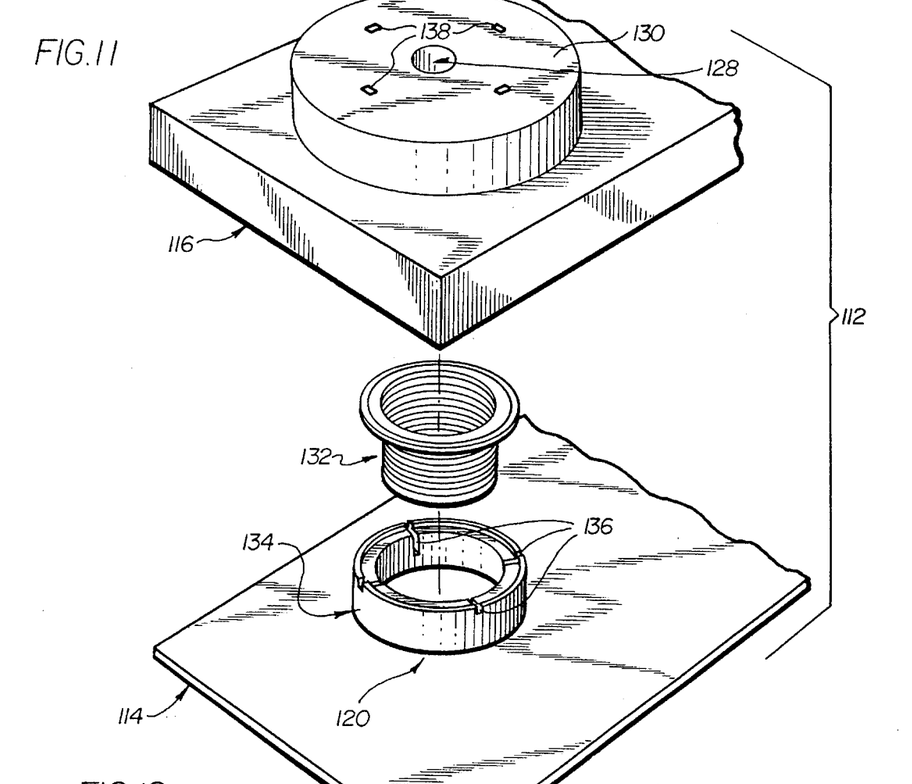
FIG. 11 is a fragmentary exploded perspective view of the pumping cartridge shown in FIGS. 8–10 (from which the lower housing has been omitted)
Figure 12:
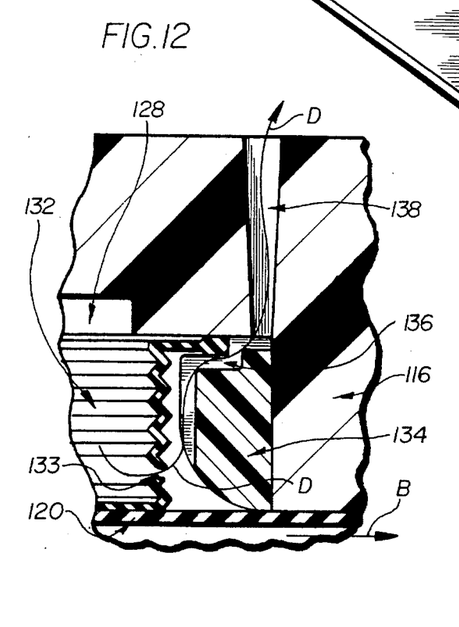
FIG. 12 is an enlarged sectional view similar to FIG. 10 showing safety vent flow of pneumatic drive air through a rupture in one of the diaphragms of the cartridge pump.
Figure 13:
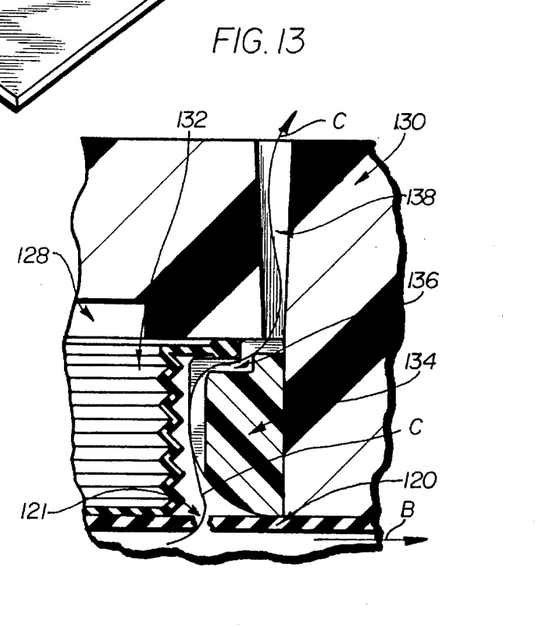
FIG. 13 is an enlarged sectional view similar to FIG. 12 showing safety vent flow of sterile fluid through a rupture in the second, fluid diaphragm of the pump structure.

In the illustrated embodiment, the secondary, pneumatic diaphragm 132 has a generally corrugated cylindrical sidewall 132a which facilitates the accordion-like oscillation and displacement of the diaphragm endwall 132b to produce pneumatic drive reciprocation against the main diaphragm pump portion 120. The pneumatic diaphragm 132 has a radially outwardly turned annular flange portion 132c which is clamped against the boss 130 by an annular seating and wear protection ring 134. The ring 134 has annularly distributed vent slots 136 which are aligned to communicate with corresponding vent channels 138 through the housing boss 130 as best shown in FIGS. 10 and 12–13.

Use of dual pumping diaphragms, pneumatic diaphragm 132 and pump diaphragm portion 120, provides a safety feature to ensure that the possibility of a rupture in either of the diaphragms cannot result in leaking of pneumatic drive gas, air or nitrogen, into the sterile fluid and ultimately the patient's body. For example, referring to FIG. 13, should the primary pump diaphragm portion 120 become ruptured at 121, the pneumatic drive gas remains retained by the pneumatic diaphragm 132 so that the gas is isolated from the sterile fluid flow path B; leaking of sterile fluid through the rupture 121 will be directed therethrough along a relief flow path C provided by the communicating vents 136 and 138 producing a visible discharge to atmosphere from the boss 130. The pneumatic diaphragm 132 thus functions as a safety barrier. In the event that the pneumatic diaphragm 132 itself ruptures as shown in FIG. 12 at 133, the pneumatic drive gas, typically air, will be vented to atmosphere through the vent slots 136 and 138 along a relief vent flow path indicated at D, so that the vented leaking air remains isolated from the sterile fluid flow path B by the pump diaphragm portion 120.

Referring to FIGS. 14–19, a third embodiment of a fluid pumping cartridge in accordance with the present invention is illustrated. In the embodiment illustrated in FIGS. 14–19, the cartridge generally designated by reference character 212 is a generally cylindrical module divided into a pump section 214 and a pulse dampening section 216 which are arranged in opposing or stacked relation within a three-piece housing 222, 224 and 226 secured, for example, by bolts 227. As diagrammatically illustrated in FIG. 15, both the pump section 214 and the pulse dampening section 216 are pneumatically (or hydraulically) actuated and controlled through respective lines 218 and 220 from manifold 217 so that the cartridge assembly 212 could be remotely disposed from the pneumatic pump drive actuator circuit 219 and dampening control regulator 221 which are more fully described hereinafter.

Referring again to FIGS. 14 and 15, the pump section 214 of the cartridge 212 is housed between a pump housing portion 222 and a fluid housing portion 224. The pulse dampening section is housed between the fluid housing 224 and the dampening housing 226. Within the pump section 214, a pneumatic diaphragm 228 and a pump diaphragm 230 are paired to separate the pumped fluid indicated by arrow F from the drive gas indicated by arrow G in FIG. 15. The pneumatic diaphragm 228 and the pump diaphragm 230 are adjacently joined along a peripheral venting ring 232 which has an annularly series of venting ports 234 as best shown in FIG. 16, so that in the event of a rupture in one of the diaphragms 228 or 230, the pressurized air or the leaking fluid will be vented out of the cartridge through the vent ports 234 instead of flowing into the chamber on the opposite side of the respective diaphragm.

Figure 9:
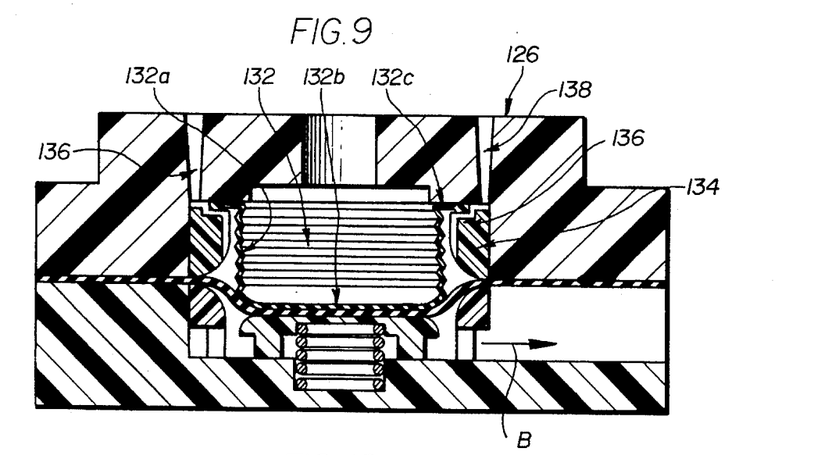
FIG. 9 is a sectional view similar to FIG. 8 showing a pumping stroke of the cartridge shown in FIG. 8.
Figure 14:
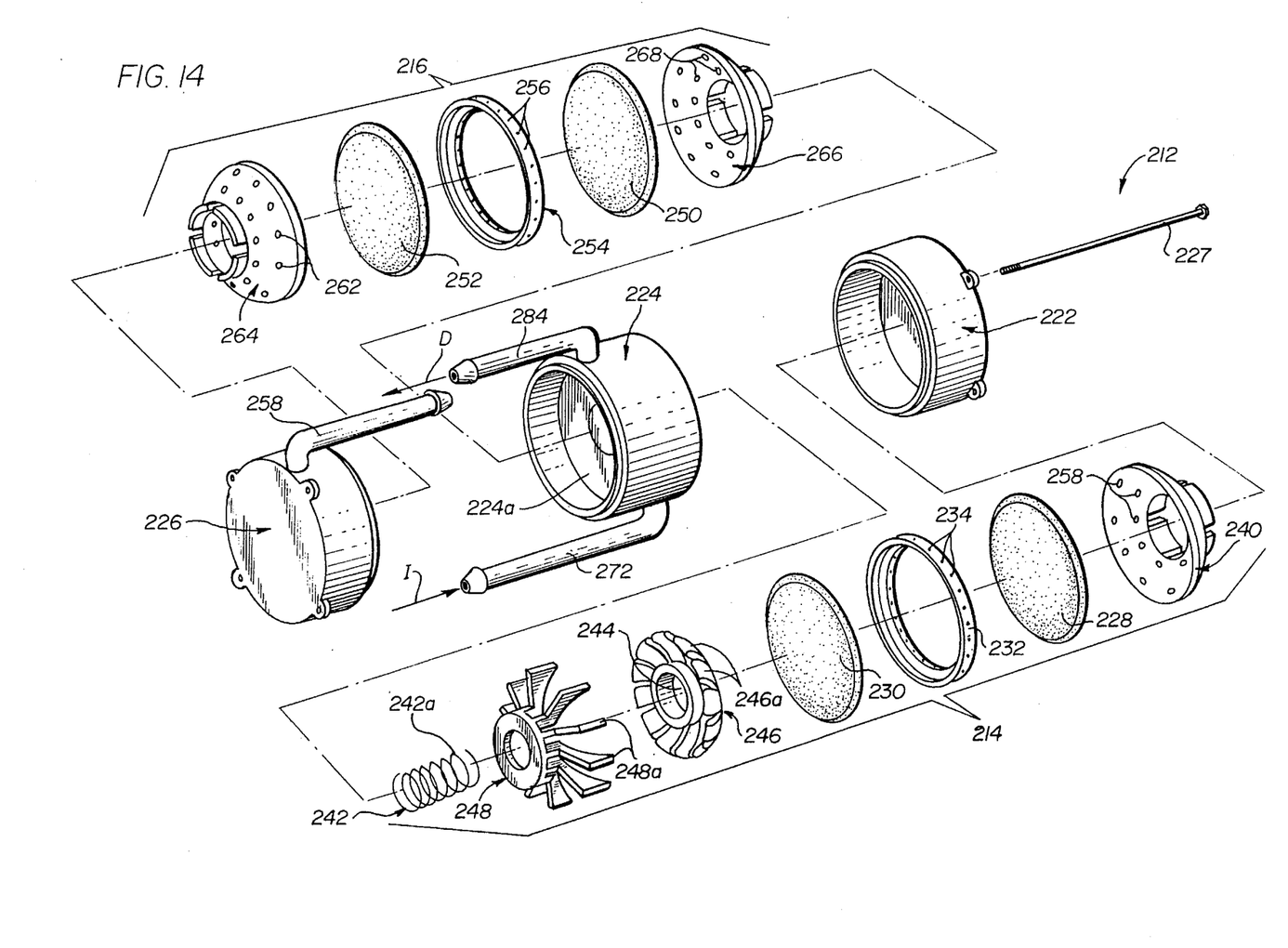
FIG. 14 is an exploded perspective view of a third embodiment of a pumping cartridge in accordance with the present invention.
Figure 18:
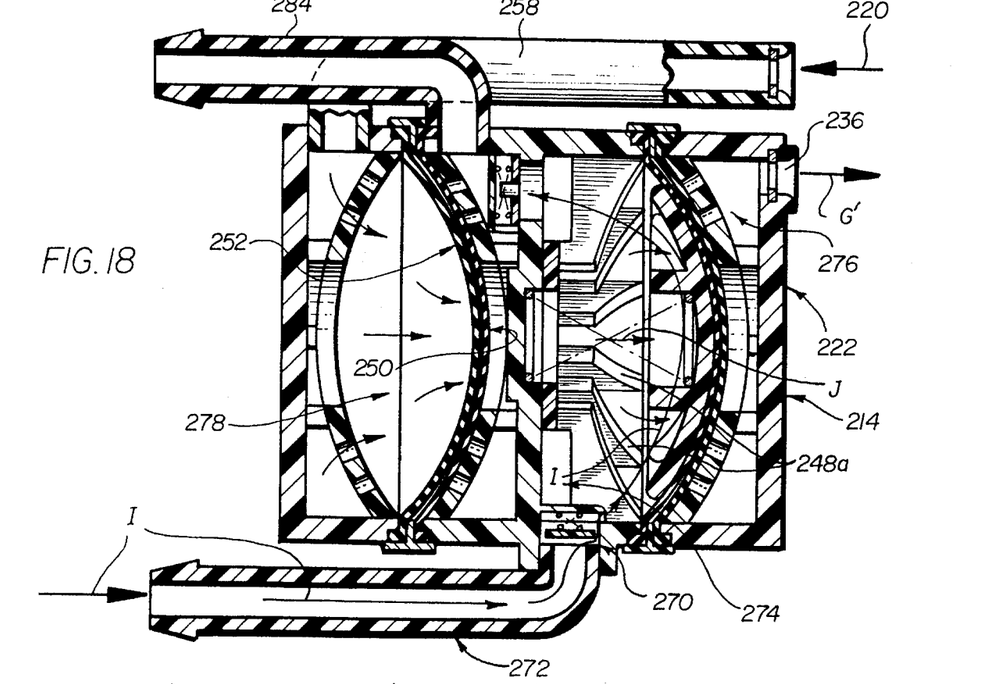
FIGS. 18 and 19 are sectional views similar to FIG. 15 showing respective fluid intake and discharge operations of both the pumping and dampening portions of the cartridge.
Figure 19:
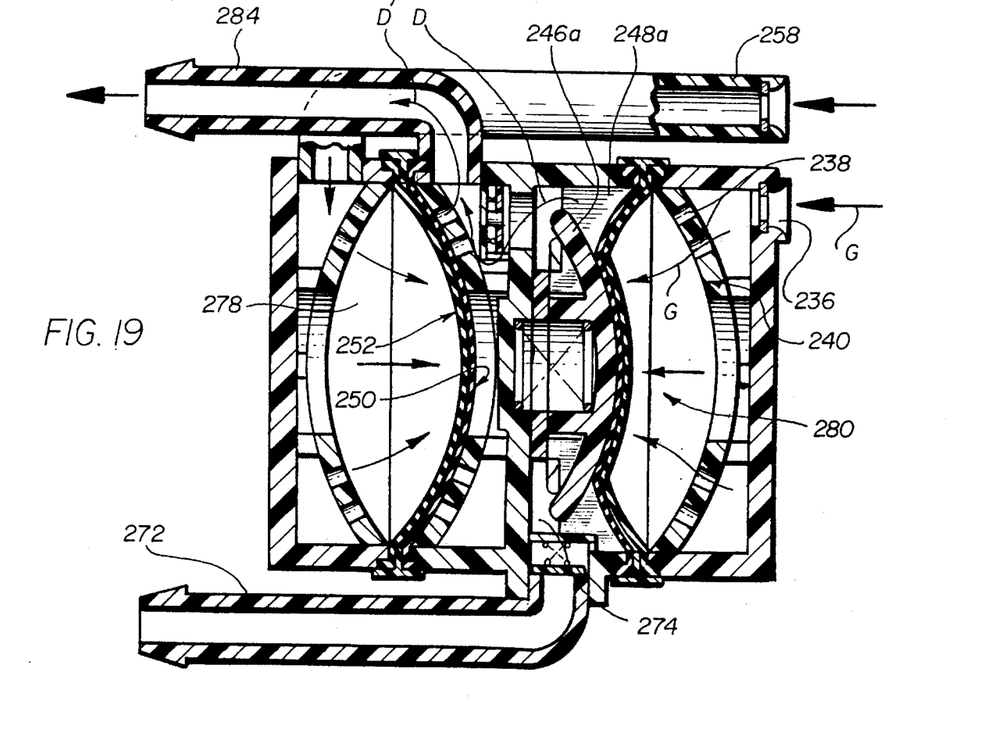

As best shown in FIGS. 18 and 19, the pump section diaphragms 228 and 230 resiliently oscillate with the cycled pneumatic pump drive pressure transmitted through line 218 through the pneumatic pump drive port 236 leading to the flow apertures 238 (FIG. 19) allowing passage through the diaphragm retainer insert 240 which is best illustrated in FIG. 14. The oscillating pump motion of the diaphragms 228 and 230 is accompanied by the reciprocating compression of the return spring 242 whose movable end 242a is secured to the central spring seat 244 of the movable diaphragm follower 246 which maintains engagement and symmetrically stabilizes the oscillating motion of the diaphragms 228 and 230 indicated by comparison of FIGS. 18 and 19 in operation of the pump section as more fully described hereinafter. The stationary pump head insert 248 is secured on the internal central wall 224a of the fluid housing 224 against which the follower 246 reaches engagement defining determination of the pump stroke as shown in FIGS. 9 and 13. In the illustrated embodiment, respective radial blades 248a and 246a allow inter-leaving of the blades to enable increase in the terminal pump stroke length as shown in FIGS. 9 and 13.

Referring again to FIG. 14, the dampening section 216 of the cartridge 212 includes another pair of diaphragms, fluid retention diaphragm 250 and dampening diaphragm 252. The fluid diaphragm 250 and dampening diaphragm 252 are peripherally joined by a venting ring 254 with an annular series of vent discharge ports 256 to provide for venting of either the pumped fluid or the pneumatic dampening air in the event of rupture in one of the diaphragms, enabling similar venting by ring 232 with reference to FIG. 16.

The dampening section 216 is pneumatically supplied with regulated air pressure along line 220 and conduit 258 through intake port 260 leading to flow passage ways 262 through diaphragm support insert 264 which is secured within the dampener housing 226 and provides a curved supporting surface for the maximum deflection of and engagement by the dampening diaphragm 252 (particularly when the pneumatic dampening pressure is discontinued). The dampener fluid diaphragm 250 is similarly restrained in maximum deflection against the curved surface of supporting insert 266 which is through apertured at 268 to enable dampening flow of the pumped fluid along paths indicated at arrows H in FIG. 15.

Figure 15:
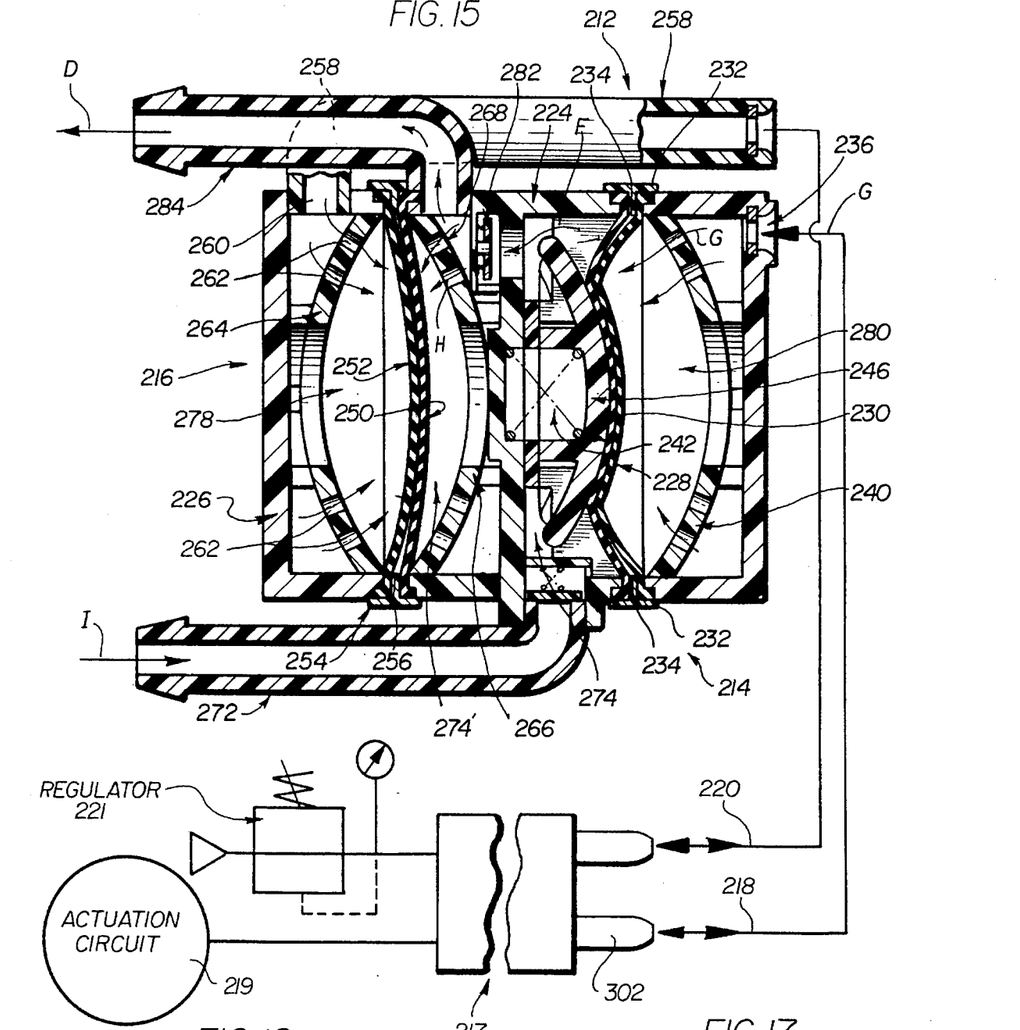
FIG. 15 is a longitudinal sectional view of the assembled pumping cartridge shown in FIG. 14, together with diagrammatic representation of pneumatic operating control of the cartridge.
Figure 16:
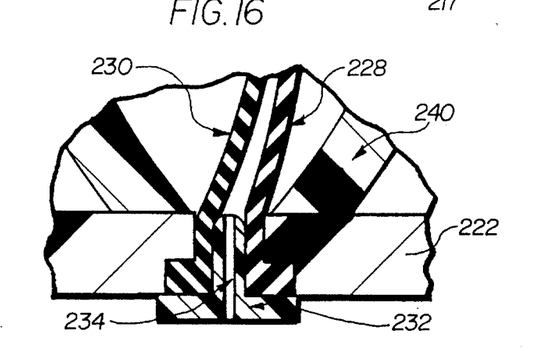
FIG. 16 is an enlarged fragmentary sectional view of a safety venting structure in the cartridge shown in FIG. 15.
Figure 17:
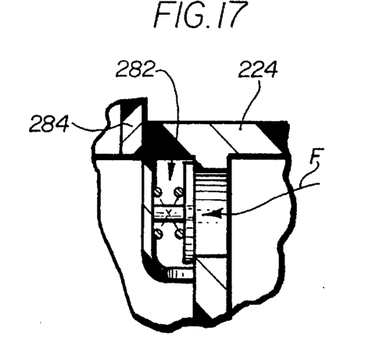
FIG. 17 is an enlarged fragmentary sectional view of a fluid discharge check valve structure in the cartridge shown in FIG. 15.

In operation, referring to FIGS. 15, 18 and 19, the cartridge pump section 214 begins an intake stroke as shown in FIG. 18 as the compressed return spring 242 expands to drive the follower 246 and the diaphragms 230 and 228 in the rightward direction as shown in FIG. 18. The resulting pressure reduction in the pump chamber 274 induces opening of the intake check valve 270 allowing entry of intake fluid flow along arrows I from supply source (not shown) through the suction conduit 272. From the open check valve 270, the intake fluid is drawn into the pump chamber 274 with flow between the vanes 248a against the follower vanes 246a along flow path indicated by arrow J. Exhausted air from the pump air chamber 276 passes through the pneumatic port 236 in the pneumatic exhaust cycle indicated by arrow G' controlled by the actuation circuit 219. Thereafter, the power stroke of the pump section 214 initiated-by the pneumatic actuator circuit 219 drives the air pressure from line 218 through the port 236 against the pneumatic diaphragm 228 along the power flow path indicated at G expanding the pump air chamber 280 as shown in FIGS. 15 and 19 and driving the pneumatic diaphragm 228 and fluid diaphragm 230 leftwardly into the fluid chamber 274, and driving the follower 246 compressing the return spring 242. The resulting compression of the pump fluid chamber 274 raises the fluid pressure sufficiently to open the discharge check valve 282 allowing fluid discharge through the discharge conduit 284 along flow paths indicated by arrows D as shown in FIGS. 15 and 19, leading to the surgical discharge handpiece (not shown).

As shown in FIG. 19, if the pneumatic pressure in the dampener chamber 278 is maintained on the dampener diaphragm 252 sufficiently high to hold the dampener diaphragm 252 and fluid diaphragm 250 against the retainer insert 266 and withstand the opposing maximum fluid pump pressure imposed on the fluid chamber side of the diaphragm 250 under control by the pneumatic regulator, the two diaphragms 250 and 252 will not deflect so that the cycled pump operation will produce a regular series of fluid flow pulses with rising and falling fluid discharge pressure from the discharge conduit 284. In this selective mode, the regulator is operated to prevent any dampening of the fluid flow pulses produced by the cycled pump operation. To maximize the intensity of the pulses, the regulated air pressure in the dampening chamber 278 is set to be as high or higher than the peak fluid pressure of the pump power stroke, and because the dampening air pressure in the chamber 278 is greater than the peak fluid pressure, the dampener diaphragms 250 and 252 act as a solid wall without dampening effect on the discharge fluid flow pulse characteristics.

Alternatively, the pneumatic dampening regulator 221 can be variably set to control the air pressure in the dampening chamber 278, for example, at approximately one-quarter to one-third of the peak fluid pressure in the fluid chamber 274 as illustrated in FIG. 15, so that as the power stroke of the pump produces fluid pressure indicated by arrows H imposed on the fluid diaphragm 250, beginning to exceed the set pressure of the pulse dampener chamber 278, diaphragms 250 and 252 will resiliently deflect leftwardly to allow a temporary increase in the volume of the fluid chamber 274'. The fluid discharge pressure is therefore limited to approximately the set pressure of the dampener chamber 278 by the pneumatic regulator.

As the pump fluid pressure falls below the dampener chamber pressure, at the end of the pump power stroke, the discharge check valve 282 closes and the air pressure in the dampener chamber 278 forces deflection of the diaphragms 252 and 250 to drive fluid out of the fluid chamber 274' (in reverse direction of the arrows H through the apertures 268) and forcing the fluid to discharge from the conduit 284 along discharge path D', enabling little or no pause in the discharge flow when a continuous fluid stream is selected.

Figure 20:
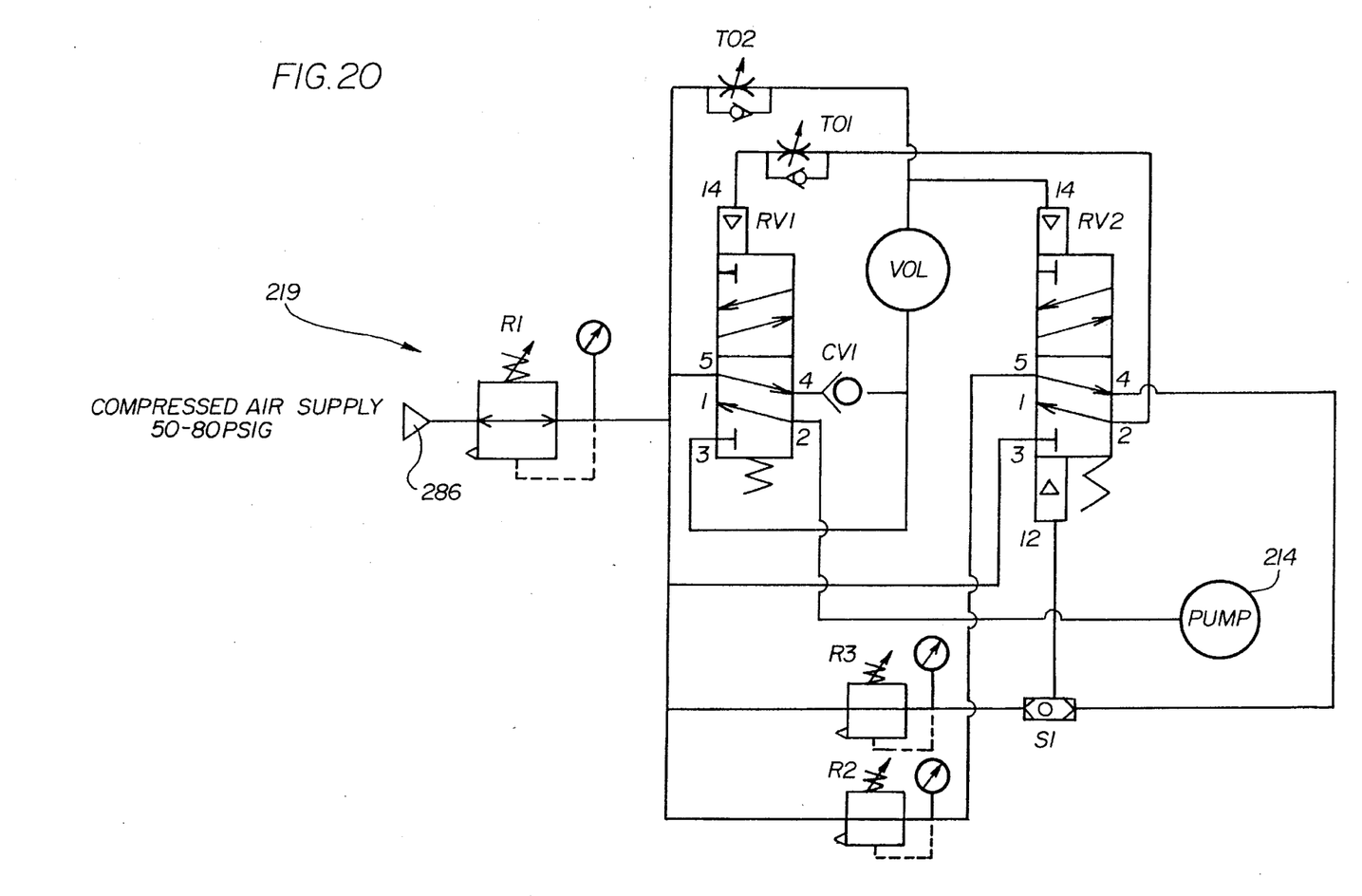
FIG. 20 is a diagrammatic pneumatic circuit for one embodiment of an actuator to drive pump operation of cartridges in accordance with the present invention.

Referring now to FIG. 20, an embodiment of a pneumatic pump actuator circuit generally designated by reference number 219 enables the surgeon to control the pneumatically reciprocating pump drive from a button on the irrigation flow handpiece and irrigation discharge valve (not shown). The cartridge pump 214 automatically begins the pneumatically reciprocating pump operation as the handpiece valve is opened.

Referring again to FIG. 20, the compressed air supply 286 is delivered through regulator R1 and the circuit 219 continues to operate pneumatic cycling of the pump 214 until interruption of flow from the pump fluid chamber 274 (FIG. 15) when the handpiece valve is closed. When fluid is prevented from leaving the pump fluid chamber, the pump air chamber volume does not correspondingly increase, therefore the pump air chamber does not drop enough to allow the valve, RV2, to shift and the cycle is stopped. As fluid is released from the pump fluid chamber, the pump air chamber pressure drops enough to allow the cycle to continue. But continuation of cycling is dependent on the pump air chamber pressure dropping for each stroke.

Detailed operation of the actuator circuit 219 is as follows:

When the operator turns on compressed air, compressed air flows through RV1 (ports 5 to 4) through CV1 (check valve), fills up all tubing connected from CV1 to RV2 port 14 and RV1 port 3. Compressed air also flows through regulator R3 and regulated air flows through shuttle valve S1 and pressurizes port 12 of RV2. Compressed air also flows through regulator R2 and regulated air flows through RV2 (ports 5 to 4), and through shuttle valve S1 and pressurizes port 12 of RV2. Note that R2 is set higher than R3, therefore the pressure at R2, port 12 at this time is the same as pressure set on RV2.

Pressure builds up in port 14 of RV2 until the force on the RV2 spool is greater than the sum of the force exerted by the pressure at RV2 port 12 plus the force exerted by the spring at the 12 end of the spool. At this point, the spool in the valve RV2 shifts.

As a result of the spool shifting in RV2, the higher air pressure on port 12 of RV2, supplied by R2, is now blocked at port 5 of RV2 and the line between S1 and port 4 of RV2 is exhausted. Pressure on port 12 of RV 2 is now the same as R3 pressure setting. Compressed air flows from port 3 to port 2 of RV2 and pressurizes TD1. TD1 begins to bleed air pressure into RV1 port 14.

Pressure in RV1 port 14 increases until the spool in RV1 shifts. As a result of the spool shifting in RV1, supply air is blocked at port 5. CV1 prevents air from being exhausted through port 1, Air flows from port 3 to port 2 of RV1, filling up the pump air volume 280, and the tubing between port 2 and the pump.

Air pressure downstream of CV1 drops in proportion to the volume that is filled. With the pump (214) off, the pressure drop is not sufficient to allow RV2 to shift, and the cycle stops.

With the pump on, the pressure drop is sufficient to allow the force on the 12 end of the spool of RV2 to overcome the force on the 14 end of the spool and RV2 shifts back to the original position.

RV2 shifting back to the original position causes the following: pressure to RV1, port 14 is exhausted, allowing RV1 to shift back to the original position, thus exhausting the pump; R3 again pressurizes RV2 port 12; and cycle continues from step 2.

TD1 controls cycle time by controlling the time interval between RV2 shifting, and RV1 shifting. R3 controls the high pressure setting that allows the highest possible pressure to be sent to the pump. TD2 sends makeup air to the system to make up for normal component leakage while in a "hold" mode (pump shut off). R2 controls the shift point of RV2 after RV1 shifts and the trapped pressure downstream of CV1 is reduced. R1 controls system pressure and is normally set at 50 PSIG.

Referring now to FIGS. 21 and 22, a second embodiment of a pneumatic actuator circuit 300 includes a two-position, five-port, four-way, detented an air piloted spool valve 310. The valve 310 is shuttled between the two positions by the presence of air pressure at the air pilot ports 312 and 314. The valve pilots are "detented" meaning that the valve will not shuttle until the air pressure is removed from one pilot and made available to the opposite pilot. When pilot 312 senses air pressure, the valve 310 shuttles to the position where the air passage between ports 1 and 2 is open and the air passage between ports 4 and 5 is simultaneously open. When the pilot 314 senses air pressure, the valve 310 shuttles to the position where air passage between ports 1 and 4 is open with simultaneous air passage opening between ports 2 and 3. Flow control valves 316 and 318 are provided to allow for a controlled air flow through respective variable orifice needle valves 316a and 318a in one direction and free flow in the opposite direction via respective internal check valves 316b and 318b.

In operation of the air drive circuit 300, a switch activates operation of a pneumatic supply source 320. For the power stroke pumping displacement of the pump diaphragm 228 (FIG. 15) the valve 310 shuttles to communicate the 1–2 position which directs pressurized air through line 322 through nozzle 302 and line 218 to the cartridge air drive port 236 (FIG. 15). As the power stroke of the pump diaphragm 228 is completed, the resulting back pressure is communicated through line 324 and the needle valve 318a whereupon sufficient pressure triggers the pilot 314. Simultaneously, the pilot 312 is exhausted through the open check valve 316b, through line 326 and through connected ports 4 and 5 of valve 310, discharging through silencer 328 to the atmosphere. Because pilot 312 is exhausted and pilot 314 is pressurized, the spool of valve 310 shuttles to connect ports 1-4 as shown in FIG. 22, to begin the return stroke of the pump diaphragm 228.

With the spool of valve 310 connecting ports 1 and 4, the pressurized air from supply 320 is directed through ports 1 and 4 to line 326 while at the same time air is exhausted from cartridge pump cavity 280 through air drive port 236, and along line 322 through connected ports 2 and 3 discharging through the silencer 328. Simultaneously, the pilot 314 is exhausted through the open check valve 318b and ports 2 and 3 of valve 310 to the silencer 328. When the pilot 312 is sufficiently pressurized through needle valve 316a from line 326, and pilot 314 exhausted, the valve 310 shuttles to again connect the 1 and 2 ports as shown in FIG. 21 and the succeeding power stroke of the cartridge pump is actuated. Adjustment of the flow control needle valves 316a and 318a, for example by rotary knob 105 (FIG. 1), enables controlled variation of the cycle rate, so that the valves 316a and 318a also function as timers for the cycled cartridge pump operation, particularly to enable variation in the pulsation frequency when pulse flow of irrigation fluid is selected.

With the exception of a conventional, electrically powered air supply, the illustrated embodiments are pneumatically controlled. Electrically operated components, such as pump drive, accumulator, and dampener control are optional modifications as well as a rotary pump in the cartridge coordinated with a selectively oscillating accumulator to produce pulse flow. Accordingly, particular embodiments of the present invention have been described herein while it will be obvious to those skilled in the art that changes and modifications in various aspects may be made without departing from the broad scope of the invention. Consequently, the scope of the invention is not limited by any particular embodiment but is defined by the appended claims and the equivalents thereof.

The Invention claimed Is:

1. A fluid pumping cartridge for particular use in delivery of sterile fluid for surgical procedures comprising:

a cartridge housing adapted for connection to and disconnection from a pump control structure;

a pump diaphragm within said cartridge housing, arranged for pumping sterile fluid therethrough;

and a separate, control diaphragm within said cartridge which is capable of resiliently oscillating and absorbing fluid flow pulses driven by said pump diaphragm in order to produce modulated flow of said sterile fluid from said cartridge.

2. A cartridge according to claim 1 further comprising conduit means for flow communication of said sterile fluid from said pump diaphragm against said control diaphragm.

3. A cartridge according to claim 2 wherein said conduit means comprises an aperture through an internal wall formed within said cartridge housing.

4. A cartridge according to claim 3 wherein said internal wall separates a pumping chamber comprising said pumping diaphragm and an accumulator chamber comprising said control diaphragm.

5. A cartridge according to claim 4 wherein said pumping chamber and accumulator chamber are arranged in adjacent relationship medially separated by said internal wall.

6. A cartridge according to claim 1 further comprising fluid dampening conduit means for directing dampening fluid against a first surface of said control diaphragm in opposition to said sterile fluid flow against a second surface of said control diaphragm in order to produce dampening by said control diaphragm of sterile fluid flow pulses imposed thereagainst from said pump diaphragm.

7. A cartridge according to claim 6 wherein said dampening conduit means comprises a dampening chamber within said cartridge housing.

8. A cartridge according to claim 1 further comprising a second control diaphragm within said cartridge arranged to engage said first mentioned control diaphragm and capable of resiliently oscillating therewith during said absorbing of fluid flow pulses.

9. A cartridge according to claim 8 further comprising a venting passageway between said first and second control diaphragms, in order to provide relief venting through said passageway for any leaking portion of said sterile fluid.

10. A cartridge according to claim 9 comprising spacing means for providing normal engagement between first and second control diaphragms and for enabling disengagement of said first and second control diaphragms to provide for said venting passageway therebetween in order to allow discharge therethrough of said leaking sterile fluid portion.

11. A cartridge according to claim 10 wherein said spacing means peripherally secures said first and second diaphragms.

12. A cartridge according to claim 11 wherein said first and second control diaphragms have circular configuration and said spacing means comprises an annular structure which circumferentially secures said first and second control diaphragms, said annular structure having one or more venting apertures therethrough communicating with said venting passageway to provide discharge of said leaking sterile fluid portion therethrough.

13. A fluid pumping cartridge for particular use in delivery of sterile fluid for surgical procedures comprising:

a cartridge housing adapted for connection to and disconnection from a pump control structure;

a pump diaphragm within said cartridge housing arranged for pumping sterile fluid therethrough;

a separate, control diaphragm within said cartridge which is capable of resiliently oscillating and absorbing fluid flow pulses driven by said pump diaphragm in order to produce modulated flow of said sterile fluid from said cartridge conduit means for flow communication of said sterile fluid from said pump diaphragm against said control diaphragm;

said conduit means comprising an aperture through an internal wall formed within said cartridge housing and medially separating a pumping chamber comprising said pumping diaphragm and an accumulator chamber comprising said control diaphragm in which said pump diaphragm and control diaphragm are opposingly oriented within said cartridge housing.

14. A fluid pumping cartridge for particular use in delivery of sterile fluid for surgical procedures comprising:

a cartridge housing adapted for connection to and disconnection from a pump control structure;

a pump diaphragm within said cartridge housing, arranged for pumping sterile fluid therethrough;

a separate, control diaphragm within said cartridge which is capable of resiliently oscillating and absorbing fluid flow pulses driven by said pump diaphragm in order to produce modulated flow of said sterile fluid from said cartridge;

fluid dampening conduit means for directing dampening fluid against a first surface of said control diaphragm in opposition to said sterile fluid flow against a second surface of said control diaphragm in order to produce dampening by said control diaphragm of sterile fluid flow pulses imposed thereagainst from said pump diaphragm; and a sterile fluid chamber having opposing chamber walls defined by said pump diaphragm and said control diaphragm.

15. A cartridge according to claim 14 wherein said sterile fluid chamber is medially arranged between said dampening chamber and a pump fluid drive chamber, such that fluid flow through said sterile fluid chamber is pumped by said pump diaphragm and modulated by said control diaphragm.

16. A fluid pumping cartridge for particular use in a single surgical procedure in order to deliver and maintain sterile condition of the pumped fluid, comprising:

a cartridge housing adapted for connection to and disconnection from a pump control structure;

a pumping chamber within said cartridge housing, said pump chamber including a pump diaphragm for pumping sterile fluid through the cartridge;

a dampening chamber formed within said cartridge housing, said dampening chamber comprising a separate control diaphragm capable of resiliently oscillating and absorbing fluid flow pulses produced by said pump diaphragm in order to produce modulated flow of said sterile fluid from said cartridge; and a sterile fluid chamber having opposing chamber walls defined by said pump diaphragm and said control diaphragm.

17. A cartridge according to claim 16 further comprising a fluid dampening conduit means in communication with said dampening chamber for directing dampening fluid against a first surface of said control diaphragm in opposition to said sterile fluid flow against a second surface of said control diaphragm in order to produce dampening by said control diaphragm of sterile fluid flow pulses imposed thereagainst from said pump diaphragm.

18. A fluid pumping cartridge for particular use in delivery of sterile fluid for surgical procedures comprising:

a cartridge housing adapted for connection to and disconnection from a pump control structure;

a pump diaphragm within said cartridge housing, arranged for pumping sterile fluid therethrough;

and a separate, control diaphragm within said cartridge which is capable of resiliently oscillating and absorbing fluid flow pulses driven by said pump diaphragm in order to produce modulated flow of said sterile fluid from said cartridge wherein said pump diaphragm and control diaphragm are opposingly oriented within said cartridge housing.

* * * * *

UNITED STATES PATENT AND TRADEMARK OFFICE
CERTIFICATE OF CORRECTION

PATENT NO. : 5,476,368
DATED : December 19, 1995
INVENTOR(S) : Richard Rabenau, Stephen P. Lisak, Terry B. Kehne and Richard M. Davis It is certified that error appears in the above-indentified patent and that said Letters Patent is hereby corrected as shown below:

Title Page:

The following reference was omitted in the Letters Patent.

[56]     References Cited
    U.S. PATENT DOCUMENTS

-- 5,129,427    7/1992 White et al ........417/540 --

Signed and Sealed this

Eleventh Day of June, 1996

*Attest:*

BRUCE LEHMAN

*Attesting Officer*              Commissioner of Patents and Trademarks